United States Patent
Grade et al.

(10) Patent No.: US 6,410,774 B1
(45) Date of Patent: Jun. 25, 2002

(54) METHOD FOR RECOVERY OF CATALYST COMPONENTS

(75) Inventors: Marsha Mottel Grade; John Yaw Ofori, both of Niskayuna; Eric James Pressman, East Greenbush, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/822,129

(22) Filed: Mar. 30, 2001

(51) Int. Cl.$^7$ .............................................. C07C 69/96
(52) U.S. Cl. ...................................... 558/274
(58) Field of Search ......................... 558/274

(56) References Cited

U.S. PATENT DOCUMENTS

| | | |
|---|---|---|
| 4,187,242 A | 2/1980 | Chalk |
| 5,231,210 A | 7/1993 | Joyce et al. |
| 5,239,106 A | 8/1993 | Shafer |
| 5,284,964 A | 2/1994 | Pressman et al. |
| 5,373,083 A | 12/1994 | King et al. |
| 5,380,907 A | 1/1995 | Mizukami et al. |
| 5,399,734 A | 3/1995 | King et al. |
| 5,498,742 A | 3/1996 | Buysch et al. |
| 5,498,789 A | 3/1996 | Takagi et al. |
| 5,502,232 A | 3/1996 | Buysch et al. |
| 5,543,547 A | 8/1996 | Iwane et al. |
| 5,625,091 A | 4/1997 | Buysch et al. |
| 5,726,340 A | 3/1998 | Takagi et al. |
| 5,760,272 A | 6/1998 | Pressman et al. |
| 5,821,377 A | 10/1998 | Buysch et al. |
| 5,856,554 A | 1/1999 | Buysch et al. |
| 5,917,078 A | 6/1999 | Battista et al. |
| 5,981,788 A | 11/1999 | Ofori et al. |
| 6,071,843 A | 6/2000 | Buysch et al. |
| 6,090,737 A | 7/2000 | Ofori |
| 6,114,564 A | 9/2000 | Pressman et al. |
| 6,143,937 A | 11/2000 | Ofori |
| 6,172,254 B1 | 1/2001 | Pressman et al. |
| 6,180,812 B1 | 1/2001 | Johnson et al. |
| 6,191,060 B1 | 2/2001 | Ofori |
| 6,191,299 B1 | 2/2001 | Pressman et al. |
| 6,197,991 B1 | 3/2001 | Spivack et al. |

FOREIGN PATENT DOCUMENTS

| | | |
|---|---|---|
| EP | 736325 | 3/1996 |
| GB | 2311777 | 10/1997 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |
| JP | 98-158221 | 6/1998 |
| JP | 98-316627 | 12/1998 |

Primary Examiner—T. A. Solola
Assistant Examiner—Joseph Murray
(74) Attorney, Agent, or Firm—S. Brude Brown; Noreen C. Johnson

(57) ABSTRACT

An integrated method is disclosed for removing and recovering a substantially water-soluble solvent and at least one metal from an organic reaction mixture comprising at least about 35% by weight aromatic hydroxy compound, which comprises the steps of: (i) contacting a reaction mixture at least once with aqueous acid, (ii) mixing the organic and aqueous phases in the presence of an oxygen source, (iii) separating the organic and aqueous phases wherein said solvent remains substantially in the organic phase; (iv) recovering metal species from the aqueous phase; and (v) recovering said solvent from the organic phase.

44 Claims, 1 Drawing Sheet

METHOD FOR RECOVERY OF CATALYST COMPONENTS

BACKGROUND OF THE INVENTION

The present invention is directed to a method for removing and recovering catalyst components from organic reaction mixtures and, more specifically, to a method for removing and recovering both metal catalyst components and substantially water-soluble solvents from organic reaction mixtures comprising carbonylation reaction products.

Aromatic carbonates find utility, inter alia, as intermediates in the preparation of polycarbonates. For example, a popular method of polycarbonate preparation is the melt transesterification of aromatic carbonates with bisphenols.

Various methods for preparing aromatic carbonates have been previously described in the literature and/or utilized by industry. A method that has enjoyed substantial popularity in the literature involves the direct carbonylation of aromatic hydroxy compounds with carbon monoxide and oxygen catalyzed by at least one Group 8, 9, or 10 metal source. Further refinements to the carbonylation catalyst composition include the identification of co-catalysts.

The utility of the carbonylation process is strongly dependent on the number of moles of aromatic carbonate produced per mole of metal catalyst utilized (i.e. "catalyst turnover number or "TON""). Consequently, much work has been directed to the identification of efficacious process and catalyst variations that increase catalyst turnover and yield of aromatic carbonate. For example, in U.S. Pat. No. 5,498,789 a catalyst system for carbonylation has been disclosed which consists of a palladium catalyst, lead compound, and an organic bromide. GB 2311777A discloses a catalyst system which comprises a palladium catalyst, a lead compound, a cobalt compound, and a halide. More efficient catalyst systems for carbonylation are reported, for example, in U.S. Pat. No. 6,114,564, 6,172,254, and 6,180,812, all assigned to the assignee of the present invention, in which catalyst systems may comprise alkali metal halides and an activating solvent (sometimes known as a "promoter compound").

Recovery and reuse of all catalyst and recyclable components from a carbonylation reaction are imperative if a process to prepare aromatic carbonates is to be economically viable and environmentally safe. In particular, all metal components from a carbonylation reaction must be recovered and recycled efficiently.

One possible method of recovery of metallic or other catalyst components comprises an aqueous extraction, for example, as is disclosed in U.S. Pat. Nos. 5,981,788 and 6,090,737, assigned to the assignee of the present invention. Although metals may be recovered by such extraction processes, nevertheless a portion of metal components is often not removed and recovered from a carbonylation reaction mixture. Recovery may be complicated by the fact that metals are often present in very low concentrations. Also, metals such as palladium and other metal co-catalysts are often present in a mixture of different oxidation states and physical phases at the end of a carbonylation reaction, making segregation of elemental species from oxidized species more likely, and thus requiring further complexity in recovery and recycle schemes. In particular insoluble metal species may be left behind in the reactor when a carbonylation reaction mixture comprising soluble metal species is removed from a reactor. It would be beneficial to remove the metal components at an early stage from a completed carbonylation reaction mixture, for example to prevent metal-promoted decomposition of the aromatic carbonate during product recovery and purification. Also, it would be desirable to have the metals all removed at one time rather than a portion in separate steps of recovery processes.

Also, when an activating solvent is present in a carbonylation reaction mixture, then the activating solvent must be recovered and recycled efficiently. Often, it is desirable to retain an activating solvent in an organic phase until it can be separated, for example by distillation. Since separation by distillation is often a high temperature process, decomposition and transesterification of aromatic carbonate product may occur, for example, if other catalyst components such as metals are present during a distillative separation of activating solvent and product. As discussed above, one possible method of removal of metallic or other catalyst components is by an aqueous extraction. In this case it is often desirable that an activating solvent remain in an organic phase during an aqueous extraction process so that it does not finally have to be separated from an aqueous stream containing other catalyst components such as metals. Many disclosed activating solvents such as polyethers tend to have a high solubility in water. A problem to be solved is to devise a method for efficient recovery of water-soluble activating solvents from complex carbonylation reaction mixtures without the necessity of separating such activating solvents from an aqueous stream. A more general problem to be solved is to devise a method of removing and recovering both metal species and activating solvent from a carbonylation reaction mixture is an integrated process.

SUMMARY OF THE INVENTION

After diligent experimentation the present inventors have discovered a method for removal and recovery of both metal species and activating solvent from complex carbonylation reaction mixtures with excellent efficiency. Thus, in one embodiment, the present invention provides a method for recovering a substantially water-soluble solvent and at least one metal from an organic reaction mixture comprising at least about 35% by weight aromatic hydroxy compound, which comprises the steps of: (i) contacting a reaction mixture at least once with aqueous acid, (ii) mixing the organic and aqueous phases in the presence of an oxygen source, (iii) separating the organic and aqueous phases wherein said solvent remains substantially in the organic phase; (iv) recovering metal species from the aqueous phase; and (v) recovering said solvent from the organic phase.

Various other features, aspects, and advantages of the present invention will become more apparent with reference to the following description and appended claims.

DETAILED DESCRIPTION OF THE INVENTION

Figure 1:
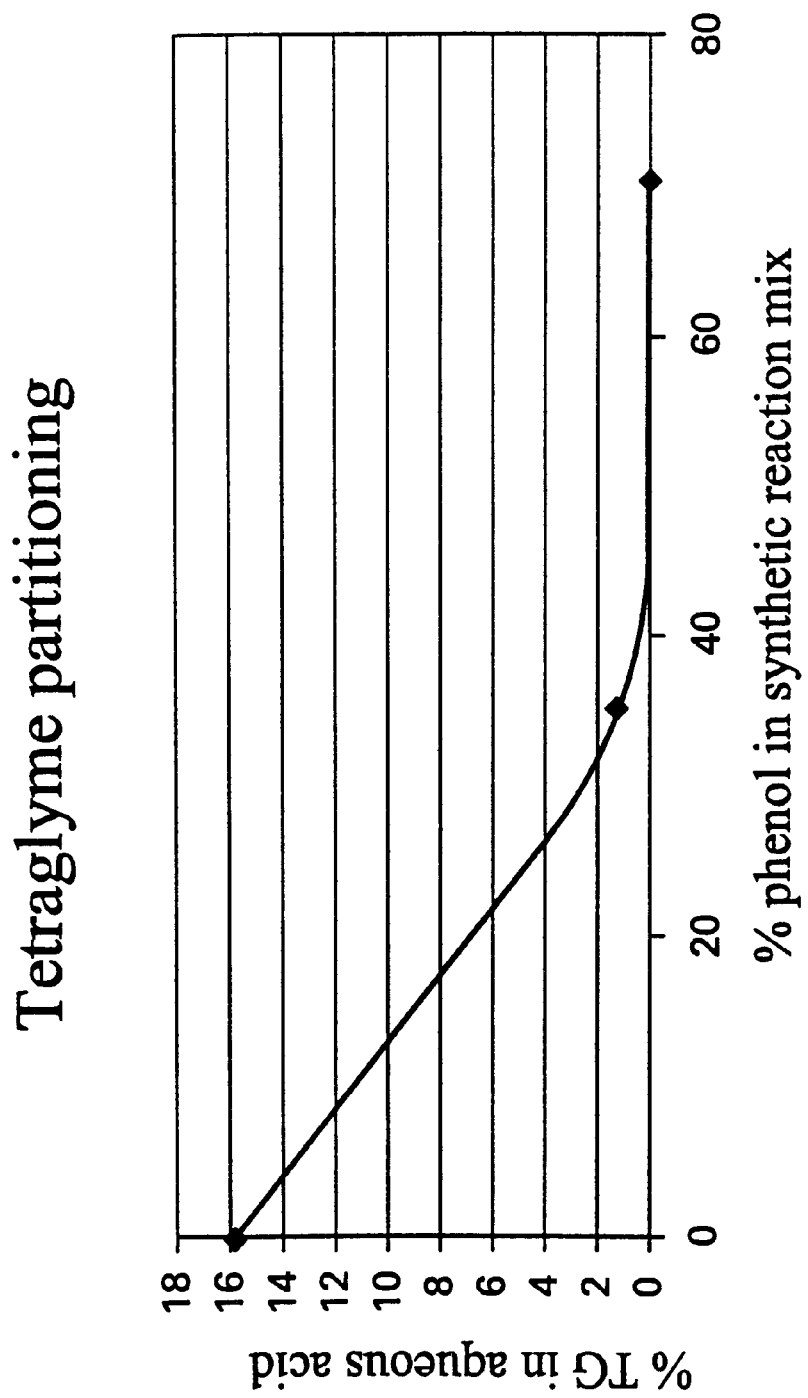
FIG. 1 is a graph of % tetraglyme (TG) remaining in an organic phase following extraction with aqueous acid as a function of % phenol in an organic phase.

Unless otherwise noted, the term "effective amount," as used herein, includes that amount of a substance capable of either increasing (directly or indirectly) the yield of the carbonylation product or increasing selectivity toward an aromatic carbonate. Effective amounts of a given substance can vary based on reaction conditions and the identity of other constituents yet can be readily determined in light of the discrete circumstances of a given application.

Any aromatic hydroxy compound convertible to a carbonate ester may be employed in carbonylation reactions of the present invention. Suitable aromatic hydroxy compounds include monocyclic, polycyclic or fused polycyclic aromatic monohydroxy or polyhydroxy compounds having from 6 to 30, and preferably from 6 to 15 carbon atoms. Illustrative examples include but are not limited to mono- and poly-hydroxy compounds such as phenol, alkylphenols, o-, m- or p-cresol, o-, m- or p-chlorophenol, o-, m- or p-ethylphenol, o-, m- or p-propylphenol, o-, m- or p-methoxyphenol, methyl salicylate, 2,6-dimethylphenol, 2,4-dimethylphenol, 3,4-dimethylphenol, 1-naphthol and 2-naphthol, xylenol, resorcinol, hydroquinone, catechol, cumenol, the various isomers of dihydroxynaphthalene, bis (4-hydroxyphenyl)propane-2,2,$\alpha,\alpha'$-bis(4-hydroxyphenyl)-p-diisopropylbenzene, and bisphenol A. Aromatic monohydroxy compounds are particularly preferred with phenol being the most preferred. In the case of substituents on the aromatic hydroxy compound, the substituents are generally 1 or 2 substituents and are preferably from C-1 to C-4 alkyl, C-1 to C-4 alkoxy, fluorine, chlorine or bromine.

When an aromatic hydroxy compound as a raw material is used as a reaction solvent in carbonylation reactions of the present invention, then another solvent need not be used. However, the mixture may also optionally contain at least one relatively inert solvent, that is a solvent whose presence does not substantially improve the yield of or selectivity toward the aromatic carbonate. Illustrative inert solvents include, but are not limited to, hexane, heptane, cyclohexane, methylene chloride, or chloroform, or an aromatic solvent such as toluene or xylene.

In various preferred embodiments, the carbonylation reaction catalyst system comprises at least one constituent from the Group 8, 9, or 10 metals or a compound thereof. A preferred Group 8, 9, or 10 metal constituent is one having an atomic number of at least 44. A particularly preferred Group 8, 9, or 10 metal constituent is an effective amount of a palladium source. In various embodiments, the palladium source may be in elemental form, or it may be employed as a palladium compound. The palladium source can be employed in a form that is substantially soluble in the reaction media or that becomes substantially soluble in the reaction mixture, or in a form which is substantially insoluble in the reaction media, such as a supported- or polymer-bound palladium source. Accordingly, palladium black or palladium deposited on carbon, palladium deposited on alumina or palladium deposited on silica may be used as well as palladium halides, palladium chloride, palladium bromide, palladium iodide; palladium sulfate; palladium nitrate, palladium carboxylates, palladium oxides, palladium acetate and palladium 2,4-pentanedionate; and palladium complexes containing carbon monoxide, amines, nitrites, nitrites, phosphines or olefins, such as $PdCl_2(PhCN)_2$ and $PdCl_2(PPh_3)_2$. As used herein, the term "complexes" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes.

In various applications, it may be preferable to utilize palladium(II) salts of organic acids, including carboxylates with $C_{2-6}$ aliphatic carboxylic acids and palladium(II) salts of β-diketones. Palladium(II) acetate and palladium(II) 2,4-pentanedionate (also know as palladium(II) acetylacetonate; $Pd(acac)_2$) are generally most preferred. Mixtures of palladium materials are also contemplated.

The quantity of the at least one Group 8, 9, or 10 metal constituent is not particularly limited in the method of the present invention. In one embodiment the amount of Group 8, 9, or 10 metal source employed is sufficient to provide a molar ratio of metal to aromatic hydroxy compound in a range of between about 1:800 and about 1:1,000,000, in another embodiment a molar ratio of metal to aromatic hydroxy compound in a range of between about 1:4000 and about 1:1,000,000 moles, in still another embodiment a molar ratio of metal to aromatic hydroxy compound in a range of between about 1:40,000 and about 1:200,000, and in yet still another embodiment a molar ratio of metal to aromatic hydroxy compound in a range of between about 1:65,000 and about 1:100,000.

There also can be used in combination with the Group 8, 9, or 10 metal constituent and catalyst system at least one quinone and aromatic diol formed by the reduction of said quinone or a mixture thereof 1,4-Bendoquinone and hydroquinone are preferred. In addition, compounds such as 1,2-quinone and catechol, anthraquinone, 9,10-dihydroxyanthracene, and phenanthrenequinone also can be used. When present, the at least one quinone and aromatic diol formed by the reduction of said quinone or a mixture thereof may be present in one embodiment in an amount in a range of between about 10 moles and about 60 moles, and in another embodiment in an amount in a range of between about 25 moles and about 40 moles of quinone and/or reduction product thereof per gram-atom of Group 8, 9, or 10 metal catalyst.

In addition to the at least one Group 8, 9, or 10 metal constituent, there is typically present in carbonylation reaction mixtures of the invention an effective amount of at least one metal co-catalyst (sometimes referred to hereinafter as inorganic co-catalyst or IOCC) containing a metal different from the at least one Group 8, 9, or 10 metal. Suitable metal co-catalysts include all those known in the art which promote formation of carbonate ester from aromatic hydroxy compound under reactive conditions in the presence of the at least one Group 8, 9, or 10 metal catalyst. Metal co-catalyst sources include elemental metals, metal compounds, and precursors thereof which may form catalytically active metal species under the reaction conditions, it being possible for use to be made of the metal in various degrees of oxidation. Metal co-catalysts may be initially soluble or partially soluble in the mixture, or initially insoluble as in supported- or polymer-bound metal co-catalyst species. Alternatively, metal co-catalysts may be initially insoluble in the mixture and form soluble metal co-catalyst species during the course of the reaction. Illustrative metal co-catalysts are disclosed in numerous patents and include, but are not limited to, either alone or in combination, lead, copper, titanium, cobalt, manganese, zinc, bismuth, zirconium, tungsten, chromium, nickel, iron, and lanthanide metals such as cerium, ytterbium and the like. Preferred metal co-catalysts include lead, copper, titanium, cobalt, manganese, and lanthanide metals such as cerium, either alone or in combination. In particularly preferred embodiments metal co-catalysts comprise compounds of lead, either used alone or in combination with at least one of a titanium source, copper source, or cerium source. In another particularly preferred embodiment metal co-catalysts comprise a mixture of at least one copper source and at least one titanium source.

The at least one metal co-catalyst can be introduced to the carbonylation reaction in various forms, including salts and complexes, such as tetradentate, pentadentate, hexadentate, heptadentate, octadentate, or nonadentate complexes. Illustrative forms may include oxides, halides, carboxylates (for example of carboxylic acids containing from 2–6 carbon atoms), diketones (including beta-diketones), nitrates, complexes containing carbon monoxide, olefins, amines, phosphines and halides, and the like. Suitable beta-diketones include those known in the art as ligands for the metal co-catalysts of the present invention. Examples include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components (such as palladium). A metal co-catalyst may be used in its elemental form if sufficient reactive surface area can be provided.

A preferred class of metal co-catalysts comprises at least one lead source (sometimes referred to hereinafter as lead compound). In preferred embodiments a lead compound is typically at least partially soluble in a liquid phase under the reaction conditions. Examples of such lead compounds include, but are not limited to, lead oxides, for example PbO, $Pb_3O_4$, and $PbO_2$; lead carboxylates, for example lead (II) acetate and lead (II) propionate; inorganic lead salts such as lead (II) nitrate and lead (II) sulfate; alkoxy and aryloxy lead compounds such as lead (II) methoxide, and lead (II) phenoxide; lead complexes such as lead (II) acetylacetonate and phthalocyanine lead, and organolead compounds (that is lead compounds having at least one lead-carbon bond) such as tetraethyl lead. Of these compounds, lead oxides and lead compounds represented by the formula $Pb(OR)_2$ wherein R is an aryl group having a carbon number from 6 to 10 are preferred. Mixtures of the aforementioned lead compounds are also contemplated.

Examples of titanium sources (sometimes referred to hereinafter as titanium compounds) include inorganic titanium salts such as titanium (IV) bromide, titanium (IV) chloride; titanium alkoxides and aryloxides such as titanium (IV) methoxide, titanium (IV) ethoxide, titanium (IV) isopropoxide, titanium (IV) 2-ethylhexoxide, titanium (IV) butoxide, titanium (IV) 2-ethyl-1,3-hexanediolate, titanium (IV) (triethanolaminato)isopropoxide and titanium (IV) phenoxide; and titanium salts of β-diketones or β-ketoesters such as titanium (IV) diisopropoxide bis(acetylacetonate), titanium (IV) bis(ethyl acetoacetato)diisopropoxide, titanium (IV) oxide bis(2,4-pentanedionate) (or titanium (IV) oxide acetylacetonate). Mixtures of titanium compounds may also be employed. The preferred titanium sources are titanium (IV) alkoxides and aryloxides such as titanium (IV) butoxide and titanium (IV) phenoxide; and salts of β-diketones or β-ketoesters such as titanium (IV) oxide acetylacetonate ($Ti(O)(acac)_2$) and titanium (IV) bis(ethyl acetoacetato)diisopropoxide.

Examples of manganese sources (sometimes referred to hereinafter as manganese compounds) include manganese halides, manganese chloride, manganese bromide, manganese nitrate, manganese carboxylates such as manganese (II) acetate, and manganese salts of β-diketones such as manganese (III) 2,4-pentanedionate and manganese (II) 2,4-pentanedionate (manganese (II) acetylacetonate). Mixtures of manganese compounds may also be employed. The preferred manganese compounds are manganese 2,4-pentanedionates.

Examples of copper sources (sometimes referred to hereinafter as copper compounds) are inorganic cupric or cuprous salts or copper complexes. Illustrative examples include, but are not limited to, copper (i) chloride, copper (I) bromide, copper (I) iodide; copper (II) chloride, copper (I) bromide, copper (II) iodide; copper carboxylates such as copper acetate, copper gluconate, and copper (II) 2-ethylhexanoate; copper (ii) hydroxide, copper alkoxides and aryloxides; copper nitrate; and copper salts of 13-diketones such as copper (11) bis(2,4-pentanedionate) (also know as copper (II) acetylacetonate; $Cu(acac)_2$). Mixtures of copper compounds may also be employed. The preferred copper compounds are 2,4-pentanedionates.

Lanthanide metals include cerium, praseodymium, neodymium, promethium, samarium, europium, gadolinium, terbium, dysprosium, holmium, erbium, thulium, ytterbium, and lutetium. Examples of lanthanide sources (sometimes referred to hereinafter as lanthanide compounds) include lanthanide carboxylates such as cerium acetate, and lanthanide salts of β-diketones such as lanthanide 2,4-pentanedionates (lanthanide acetylacetonates) or lanthanide hexafluoroacetylacetonates. Mixtures of lanthanide compounds may also be employed. In one embodiment preferred lanthanide compounds are cerium compounds including cerium carboxylates such as cerium acetate, and cerium salts of β-diketones such as cerium (III) 2,4-pentanedionate (cerium (III) acetylacetonate). Mixtures of cerium compounds may also be employed. The preferred cerium compounds are cerium 2,4-pentanedionates.

Examples of cobalt sources (sometimes referred to hereinafter as cobalt compounds) include cobalt (II) halide or carboxylate salts, such as cobalt chloride and cobalt acetate. Preferred cobalt sources include compounds of the type disclosed in U.S. Pat. No. 5,231,210, namely, complexes of cobalt(II) salts with organic compounds capable of forming complexes, especially pentadentate complexes, therewith. illustrative organic compounds of this type are nitrogen-containing heterocyclic compounds including pyridines, bipyridines, terpyridines, quinolines, isoquinolines and biquinolines; aliphatic polyamines such as ethylenediamine and tetraalkylethylenediamines, such as tetramethylethylenediatrine; crown ethers; aliphatic ethers; aromatic or aliphatic amine ethers such as cryptands; and Schiff bases. An especially preferred cobalt source is cobalt(II) salt of bis[3-(salicylalamino)-propyl]methylamine, sometimes known as "CoSMDPT".

IOCC's are included in the carbonylation reaction catalyst system in effective amounts. In this context an "effective amount" is an amount of IOCC (or combination of IOCC's) that increases the number of moles of aromatic carbonate produced per mole of Group 8, 9, or 10 metal utilized; increases the number of moles of aromatic carbonate produced per mole of salt utilized; or increases selectivity toward aromatic carbonate production beyond that obtained in the absence of the IOCC (or combination of IOCC's). Effective amounts of an IOCC in a given application will depend on various factors, such as the identity of reactants and reaction conditions. In one embodiment at least one IOCC is present in an amount in a range of between about 0.1 gram-atoms of metal and about 200 gram-atoms of metal per gram-atom of the Group 8, 9, or 10 metal, in another embodiment in a range of between about 1 gram-atom of metal and about 150 gram-atoms of metal per gram-atom of the Group 8, 9, or 10 metal, and in still another embodiment in a range of between about 2 gram-atoms of metal and about 100 gram-atoms of metal per gram-atom of the Group 8, 9, or 10 metal. For example, when palladium is included in the reaction, the molar ratio of lead relative to palladium at the initiation of the reaction in one embodiment is in a range of between about 0.1 and about 150, in another embodiment in a range of between about 1 and about 100, and in still another embodiment in a range of between about 5 and about 100. In yet still another embodiment the molar ratio of lead relative to palladium at the initiation of the reaction is greater than about 17. In yet still another embodiment the molar ratio of lead relative to palladium at the initiation of the reaction is in a range of between about 25 and about 100.

At least one base may optionally be present in carbonylation reaction mixtures of the present invention. Any effective bases or mixtures thereof, whether organic or inorganic may be used in the process of the invention. In preferred embodiments a base is used which is capable of generating the conjugate base of an aromatic hydroxy compound and not interfering with the function of any catalyst component. Illustrative examples of inorganic bases include, but are not limited to, alkali metal hydroxides and alkali metal carbonates, alkali metal carboxylates or other salts of weak acids or alkali metal salts of aromatic hydroxy compounds, for example alkali metal phenoxides. Obviously, the hydrates of alkali metal phenoxides can also be used in the process. An example of such a hydrate which may be mentioned is sodium phenoxide trihydrate. In general the use of hydrates and the concomitant addition of water to the mixture may lead, inter alia, to poorer conversion rates and decomposition of carbonates formed. Illustrative examples of organic bases include, but are not limited to, onium hydroxides, onium phenoxides, ammonium hydroxides, ammonium phenoxides, phosphonium hydroxides, phosphonium phenoxides, sulfonium hydroxides, sulfonium phenoxides, guanidinium hydroxides, guanidinium phenoxides, tertiary amines which bear as organic radicals $C_6$–$C_{10}$ aryl, $C_6$–$C_{12}$ aralkyl and/or $C_1$–$C_{20}$-alkyl or represent pyridine bases or hydrogenated pyridine bases; for example dimethylbutylamine, triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6-pentamethylpiperidine. The base used is preferably an alkali metal salt of an aromatic hydroxy compound, particularly preferably an alkali metal salt of the aromatic hydroxy compound which is also to be converted to the organic carbonate. These alkali metal salts can be lithium salts, sodium salts, potassium salts, rubidium salts or cesium salts. Lithium phenoxide, sodium phenoxide and potassium phenoxide are preferably used; sodium phenoxide is particularly preferred.

A base may be added as a pure compound or as a precursor compound, such as addition of an alkali metal-comprising base as a precursor for an alkali metal salt of the aromatic hydroxy compound which is also to be converted to the organic carbonate. Illustrative alkali metal-comprising bases include, but are not limited to, sodium hydroxide, and sodium salts of weak acids such as sodium carboxylates, sodium acetate, and sodium acetylacetonate. A base may be added to the mixture in any convenient form, such as in solid form or as a liquid or a melt, either in neat form or in a solution. In a further embodiment of the invention, the base is added to the mixture as a solution which contains an amount in a range of between about 0.1% and about 80% by weight of base, in another embodiment an amount in a range of between about 0.5% and about 65% by weight of base, and in still another embodiment an amount in a range of between about 1% and about 50% by weight of base. The solvents which may optionally be used in this context include aromatic hydroxy compounds, such as the aromatic hydroxy compound to be reacted, particularly phenol, and inert solvents. Examples of solvents which may be mentioned are dimethylacetamide, N-methylpyrrolidinone, dioxane, tetramethylurea, halogenated hydrocarbons (e.g. chlorobenzene or dichlorobenzene) and ethers, such as tetraethylene glycol dimethyl ether. The solvents may be used alone or in any combination with each other.

A base, if used, is added in an amount independent of the stoichiometry. The ratio of base to Group 8, 9, or 10 metal is preferably chosen in such away that at least one base is present in an amount in a range of between about 0.1 molar equivalent and about 2500 molar equivalents of base based on Group 8, 9, or 10 metal, in another embodiment in a range of between about 5 molar equivalents and about 1500 molar equivalents of base based on Group 8, 9, or 10 metal, in still another embodiment in a range of between about 50 molar equivalents and about 1000 molar equivalents of base based on Group 8, 9, or 10 metal, and in still another embodiment in a range of between about 100 molar equivalents and about 400 molar equivalents of base based on Group 8, 9, or 10 metal.

The catalyst system employed in carbonylation reactions of the present invention contains at least one salt with anion selected from tetrafluoroborates, hexafluorophosphates, nitrates, carboxylates, benzoates, acetates, sulfates, tetraaryl borates, aryl sulfonates, alkyl sulfonates, and halides. In preferred embodiments, the cation portion of the salt may be chosen from alkali metal cations. Accordingly, a non-exclusive listing of preferred alkali metal salts includes those with anions listed hereinabove, such as lithium bromide, sodium chloride, sodium bromide, potassium chloride, potassium bromide, and cesium bromide.

Mixtures of the aforementioned salts are also suitable for use in the invention. In one embodiment at least one salt is present in the mixture in an amount in a range of between about 1 mole and about 2000 moles per gram-atom of Group 8, 9,or 10 metal catalyst, in another embodiment in an amount in a range of between about 2 moles and about 1500 moles per gram-atom of Group 8, 9, or 10 metal catalyst, and in still another embodiment in an amount in a range of between about 5 moles and about 1000 moles per gram-atom of Group 8, 9, or 10 metal catalyst.

The catalyst system in carbonylation reaction mixtures of the invention includes an effective amount of at least one activating organic solvent. Preferred activating organic solvents include polyethers; i.e., compounds containing two or more C—O—C linkages, for example as is disclosed in U.S. Pat. No. 6,114,564. The polyether used is preferably free from hydroxy groups to maximize its desired activity and avoid competition with the aromatic hydroxy compound in the carbonylation reaction. Preferred polyethers contain two or more (O—C—C) units.

The polyether may be aliphatic or mixed aliphatic-aromatic. As used in the identification of the polyether, the term "aliphatic" refers to the structures of hydrocarbon groups within the molecule, not to the overall structure of the molecule. Thus, "aliphatic polyether" includes heterocyclic polyether molecules containing aliphatic groups within their molecular structure. Suitable aliphatic polyethers include diethylene glycol dialkyl ethers such as diethylene glycol dimethyl ether (hereinafter "diglyme"), triethylene glycol dialkyl ethers such as triethylene glycol dimethyl ether (hereinafter "triglyme"), tetraethylene glycol dialkyl ethers such as tetraethylene glycol dimethyl ether (hereinafter "tetraglyme"), polyethylene glycol dialkyl ethers such as polyethylene glycol dimethyl ether and crown ethers such as 15-crown-5 (1,4,7,10,13-pentaoxacyclopentadecane) and 18-crown-6 (1,4,7,10,13, 16-hexaoxacyclooctadecane). Illustrative mixed aliphatic-aromatic polyethers include diethylene glycol diphenyl ether and benzo- 18-crown-6.

In alternative embodiments, the activating organic solvent can be a nitrile, for example as is disclosed in U.S. Pat. No. 6,172,254. Suitable nitrile solvents for the present method include $C_{2-8}$ aliphatic or $C_{7-10}$ aromatic mono- or dinitriles. Illustrative mononitriles include acetonitrile, propionitrile, and benzonitrile. Illustrative dinitriles include succinonitrile, adiponitrile, and benzodinitrile. Mononitriles are generally preferred; more specifically preferred is acetonitrile.

In further alternative embodiments, the activating organic solvent can be a carboxylic acid amide, for example as is disclosed in U.S. Pat. No. 6,180,812. Fully substituted amides (containing no NH groups including the amide nitrogen) are preferred. Aliphatic, aromatic or heterocyclic amides may be used. Illustrative amides are dimethylformamide, dimethylacetamide (hereinafter sometimes "DMA"), dimethylbenzamide and N-methylpyrrolidinone (NMP). Particularly preferred are NMP and DMA.

The activating organic solvent can be a sulfone, which may be aliphatic, aromatic or heterocyclic. Illustrative sulfones are dimethyl sulfone, diethyl sulfone, diphenyl sulfone and sulfolane (tetrahydrothiophene-1,1-dioxide). Of these, sulfolane is often preferred.

Carbonylation reaction mixtures may comprise mixtures of activating solvents from the same genus and also mixtures of activating solvents from different genus's as described above. In one preferred embodiment activating solvents are substantially water-soluble in the absence of other carbonylation reaction components, meaning that activating solvent is at least about 90% soluble in water or that water is at least about 90% soluble in activating solvent at ambient temperature. In another preferred embodiment activating solvents are essentially completely miscible with water in the absence of other carbonylation reaction components. The water miscibility characteristics of activating solvents may be readily determined, for example, by simple experimentation or by reference to standard reference works such as the CRC Handbook of Chemistry and Physics.

It is noted that the function of the optional activating organic solvent in various embodiments of the invention is not that of an inert solvent. Rather, the activating organic solvent is an active catalyst component that improves the yield of or selectivity toward the aromatic carbonate. The role of the activating organic solvent is believed to be to increase the degree of dissociation and ionization of salt composition perhaps by forming a complex with the cationic portion of said component, although the invention is in no way dependent on this or any other theory of operation. The amount of activating organic solvent employed will be an amount effective to optimize aromatic carbonate formation, in general by increasing the yield of the desired aromatic carbonate as evidenced, for example, by an increase in "turnover number"; i.e., the number of moles of aromatic carbonate formed per gram-atom of the Group 8, 9, or 10 metal catalyst component present. In one embodiment this amount is in a range of between about 1% and about 60% by volume, in another embodiment in a range of between about 1% and about 25% by volume, in still another embodiment in a range of between about 2% and about 15% by volume, in still another embodiment in a range of between about 4% and about 12% by volume, and in yet still another embodiment in a range of between about 6% and about 8% by volume based on the total of aromatic hydroxy compound and activating organic solvent.

The amount of activating organic solvent may, however, typically depend to some extent on the salt composition and the complexing ability of the activating organic solvent employed. Crown ethers, for example, have a very high complexing tendency with metal cations. For example, 15-crown-5 complexes efficiently with sodium and 18-crown-6 with potassium. Such compounds may be used in amounts as low as an equimolar amount or less based on salt composition. Other compounds useful as activating organic solvent, such as straight chain polyethers (e.g., diglyme), may be optimally effective at much higher levels. The preferred proportion of any specific material used as activating organic solvent can be determined by simple experimentation.

The carbonylation reaction can be carried out under batch conditions or under continuous or semi-continuous conditions in reactor systems comprising one or more reaction vessels. Reaction vessels suitable for use in the method according to the invention with either homogeneous or heterogeneous catalysts include stirrer vessels, autoclaves and bubble columns, it being possible for these to be employed as individual reactors or as a cascade. In a cascade 2 to 15, preferably 2 to 10, and particularly preferably 2 to 5, reactors may be connected in series.

The reaction gases are not subject to special purity requirements but care must be taken to ensure that no catalyst poisons such as sulfur or compounds thereof are introduced. In a preferred embodiment pure carbon monoxide and pure oxygen are used. Carbon monoxide and oxygen can be introduced as a mixture or in a preferred embodiment, carbon monoxide and oxygen may be added independently of each other. When a reactor cascade is used instead of an individual reactor, the separate oxygen addition preferably proceeds in such a way that the optimal oxygen concentration is ensured in each of the reactors.

The compositions of the reaction gases carbon monoxide and oxygen can be varied in broad concentration ranges. In one embodiment a molar ratio of carbon monoxide: oxygen (normalized on carbon monoxide) is employed in a range of between about 1:0.001 and about 1:1, in another embodiment in a range of between about 1:0.01 and about 1:0.5, and in still another embodiment in a range of between about 1:0.02 and about 1:0.3. A total pressure is employed in one embodiment in the range of between about 0.1013 megapascals and about 50.6625 megapascals, in another embodiment in a range of between about 0.3447 megapascals and about 25.33 megapascals, in still another embodiment in a range of between about 1.013 megapascals and about 17.2369 megapascals, and in still another embodiment in a range of between about 1.013 megapascals and about 15.1987 megapascals.

The carbon monoxide may be high-purity carbon monoxide or carbon monoxide diluted with another gas which has no negative effects on the reaction, such as nitrogen, noble gases, or argon. The oxygen used in the present invention may be high purity oxygen, air, or, optionally, oxygen diluted with any other gas which has no negative effects on the reaction, such as nitrogen, noble gases, or argon. The concentration of inert gas in the reaction gas may be in one embodiment an amount in a range of between 0 and about 60 volume %, in another embodiment an amount in a range of between 0 and about 20 volume %, and in still another embodiment an amount in a range of between 0 and about 5 volume %. The concentration of 0 volume % represents the special case of the preferred state which is free of inert gas.

In a further preferred embodiment carbon monoxide and oxygen may be added independently of each other. The oxygen addition, in this case, can take place, if desired, together with inert gas. When a reactor cascade is used instead of an individual reactor, the separate oxygen addition preferably proceeds in such a way that the optimal oxygen concentration is ensured in each of the reactors.

The reaction gas, comprising carbon monoxide, oxygen and, optionally, an inert gas, may be introduced at a rate in one embodiment in a range of between about 1 liter and about 100,000 liters (S.T.P.) per liter of reaction solution per hour, in another embodiment in a range of between about 5 liters and about 50,000 liters (S.T.P.) per liter of reaction solution per hour, and in still another embodiment in a range of between about 10 liters and about 10,000 liters (S.T.P.) per liter of reaction solution per hour.

Provision may be made for including a drying agent or a drying process step in the overall reaction method. Higher catalyst turnover numbers are typically obtained if water is removed from the reaction mixture during the reaction. For example, drying agents, typically molecular sieves, may be present in the reaction vessel as described, for example, in U.S. Pat. Nos. 5,399,734 and 6,191,299, both assigned to the assignee of the present invention. In another embodiment, a drying process step is included in the reaction method, such as a continuous method, for example, in U.S. Pat. Nos. 5,498,742 and 5,625,091, and in 5,917,078 which is assigned to the assignee of the present invention.

In one embodiment ultimate reaction temperatures above about 50° C. are employed, while in another embodiment ultimate reaction temperatures above about 70° C. are employed, and in still another embodiment ultimate reaction temperatures above about 80° C. are employed. In various embodiments ultimate reaction temperatures are in a range of between about 50° C. and about 150° C. In other embodiments ultimate reaction temperatures above about 90° C. are employed, with ultimate reaction temperatures in a range of between about 90° C. and about 110° C. being employed in still other embodiments. Gas sparging or mixing can be used to aid the reaction.

In one embodiment the present invention comprises an integrated method for removing and recovering a substantially water-soluble solvent and at least one metal from an organic reaction mixture comprising at least about 35% by weight aromatic hydroxy compound, which comprises the steps of: (i) contacting a reaction mixture at least once with aqueous acid, (ii) mixing the organic and aqueous phases in the presence of an oxygen source, (iii) separating the organic and aqueous phases wherein said solvent remains substantially in the organic phase; (iv) recovering metal species from the aqueous phase; and (v) recovering said solvent from the organic phase. The method, sometimes referred to hereinafter as oxidative extraction, results in more efficient removal of metal species into an aqueous, acidic phase while a substantial portion of a substantially water-soluble activating solvent remains in an organic phase. Activating solvent remaining in an organic phase may then be separated and recovered by such common methods as distillation. An oxidative extraction is performed at least one time, and may be performed more than one time on a reaction mixture, if so desired. Thus, in one embodiment an oxidative extraction is performed twice on a reaction mixture.

It has been surprisingly found that a substantially water-soluble activating solvent present in a carbonylation reaction mixture remains substantially in the organic phase upon extraction with aqueous acid when the level of aromatic hydroxy compound present in the reaction mixture is in one embodiment at least about 35% by weight, in another embodiment at least about 40% by weight, in still another embodiment at least about 45% by weight, in still another embodiment at least about 50% by weight, in still another embodiment at least about 55% by weight, in still another embodiment at least about 60% by weight, in still another embodiment at least about 65% by weight, and in yet still another embodiment at least about 70% by weight. In the present context substantially in the organic phase means that in one embodiment greater than about 90%, in another embodiment greater than about 94%, in still another embodiment greater than about 96%, in still another embodiment greater than about 98%, and in yet still another embodiment greater than about 99% by weight of the activating solvent remains in the organic phase. In still another embodiment essentially all the activating solvent remains in the organic phase following extraction with aqueous acid, as determined by common analytical methods, for example gas chromatography (GC) or high performance liquid chromatography (HPLC). In an illustrative example a polyether such as tetraglyme was found to remain essentially completely in an organic phase of a carbonylation reaction mixture comprising diphenyl carbonate and at least about 40% phenol following aqueous acid extraction. It was anticipated that a substantial portion of tetraglyme would transfer to the aqueous phase since tetraglyme has essentially infinite solubility in water.

The levels of metals removed from a carbonylation reaction mixture by oxidative extraction are typically enhanced compared to the levels removed in the absence of an oxygen source. Depending upon such factors as type of metal, the level of any metal removed is typically a substantial portion and is in one embodiment greater than about 50%, in another embodiment greater than about 75%, in still another embodiment greater than about 80%, in still another embodiment greater than about 85%, in still another embodiment greater than about 90%, in still another embodiment greater than about 95%, in still another embodiment greater than about 98%, and in yet still another embodiment greater than about 99% of the metal's initial level in a carbonylation reaction mixture. In another embodiment the level of any metal removed is essentially 100% of its initial level in a carbonylation reaction mixture, meaning either that no detectable level of metal remains in a carbonylation reaction mixture or that essentially all the metal is accounted for by analysis of the aqueous phase, in both cases as determined by common analytical methods, such as AA or ICP. In illustrative examples a single oxidative extraction of a carbonylation reaction mixture comprising a Pd/Pb catalyst system may typically remove about 90% of the initial level of Pd and greater than 98% of the initial level of Pb from an organic phase into the aqueous phase. Similarly, oxidative extractions of various carbonylation reaction mixtures comprising Pd/Cu/Ti catalyst packages may typically remove an amount in a range of between about 80% and about 90% of the initial level of Pd, an amount in a range of between about 85% and about 100% of the initial level of Cu and an amount in a range of between about 90% and about 100% of the initial level of Ti from an organic phase into the aqueous phase.

Oxygen sources which may be used in the method of the present invention include pure oxygen and oxygen diluted with any other gas which has no negative effects on the reaction mixture constituents, such as nitrogen, noble gases, or argon. In one embodiment air is employed as an oxygen source. The concentration of inert gas in the oxygen source may be in one embodiment an amount in a range of between 0 and about 99 volume % and in another embodiment an amount in a range of between 0 and about 75 volume %. The concentration of 0 volume % represents the special case which is free of inert gas.

An oxygen source may be provided in the process of the invention by methods known in the art, such as by sparging the mixture with a gaseous oxygen source or by providing an atmosphere comprising oxygen in a head-space above a mixture in a reactor. In one embodiment sparging with a gaseous oxygen source serves also for mixing. In a preferred embodiment an oxygen source is provided along with a separate means of mixing. Means of mixing include those known in the art, including mechanical mixing, magnetic mixing, tumble mixing, counter-current mixing and the like. The use of static mixers is also contemplated.

Acids suitable for use in aqueous extraction include organic acids, particularly strong organic acids, such as methanesulfonic acid or trifluoroacetic acid, and inorganic acids. Suitable inorganic acids include those commonly known in the art such as hydrochloric acid and hydrobromic acid. In one preferred embodiment an acid comprises a counterion which is identical to the anion of a salt included in the carbonylation reaction mixture, for example the use of hydrochloric acid when an alkali metal chloride is present in a carbonylation reaction mixture and hydrobromic acid when an alkali metal bromide is present in a carbonylation reaction mixture. The method of the invention encompasses acids which comprise mixtures of organic acids or mixtures of inorganic acids, and also mixtures of organic acids with inorganic acids. The concentration of acid in aqueous solution is in one embodiment in a range of between about 0.5% and about 20% by weight, in another embodiment in a range of between about 0.5% and about 15% by weight, in still another embodiment in a range of between about 0.5% and about 12% by weight, and in yet still another embodiment in a range of between about 0.5% and about 10% by weight.

Depending upon such factors as the concentration and type of aromatic hydroxy compound present in a carbonylation reaction mixture, an aqueous acid extraction is typically performed at a temperature above room temperature. In one embodiment an aqueous acid extraction is performed at a temperature in a range between that temperature at which the carbonylation reaction mixture is substantially liquid and that temperature at which a component of a carbonylation reaction mixture volatilizes. In preferred embodiments an aqueous acid extraction is performed at a temperature in a range between about the melting point of the aromatic hydroxy compound and that temperature at which a component of a carbonylation reaction mixture volatilizes. In one embodiment the aromatic hydroxy compound is phenol and an aqueous acid extraction is performed at a temperature in a range of between about 40° C. and about 150° C., in another embodiment at a temperature in a range of between about 50° C. and about 100° C., and in still another embodiment at a temperature in a range of between about 60° C. and about 90° C.

Although the method is not dependent upon theory, it is believed that mixing a carbonylation reaction mixture and an aqueous acid in the presence of an oxygen source oxidizes insoluble metal species, such as elemental metals, to oxidized metal species which may then be soluble, particularly in an aqueous phase. In one embodiment the reaction mixture is contacted with aqueous acid at least once in the carbonylation reactor before transferring the reaction mixture to some other vessel. Contacting with aqueous acid in a carbonylation reactor in the presence of an oxygen source suppresses loss of metal species, particularly metal species, that often remain behind in a carbonylation reactor when a carbonylation reaction mixture is transferred out of a reactor before contacting with aqueous acid.

The time of mixing a carbonylation reaction mixture with aqueous acid is in one embodiment less than about 60 minutes, in another embodiment less than about 30 minutes, in still another embodiment less than about 20 minutes, in still another embodiment less than about 10 minutes, in still another embodiment less than about 5 minutes, and in yet still another embodiment less than about 2 minutes. Thus, in one embodiment oxidative extraction is performed in a carbonylation reactor for a time sufficient to convert at least a portion of elemental metal species to oxidized metal species. In another embodiment oxidative extraction is performed in a carbonylation reactor for a time sufficient to convert at least a portion of insoluble metal species to soluble metal species. In still another embodiment oxidative extraction is performed in a carbonylation reactor for a time sufficient to enhance the concentration of metal species in an aqueous phase. In this context enhancement of the concentration of metal species in an aqueous phase may be determined by comparing concentrations of metal species in aqueous phases derived from contact with carbonylation reaction mixtures in the presence of an oxygen source versus in the absence of an oxygen source. In an illustrative example it has been discovered that contacting a carbonylation reaction mixture comprising diphenyl carbonate with aqueous acid in the presence of an oxygen source results in enhanced removal of metal species to the aqueous phase compared to the same process carried out independently under nitrogen.

Either before or after at least one oxidative extraction, a carbonylation reaction mixture may be subjected to other purification or recovery steps. Common purification or recovery steps for carbonylation reaction mixtures are well-known to those skilled in the art and often comprise at least one filtration step. After at least one oxidative extraction, a carbonylation reaction mixture (that is, the organic phase remaining following extraction) may be subjected to other purification or recovery steps which may comprise at least one step for separating constituents comprising aromatic hydroxy compound and aromatic carbonate. In an illustrative example a carbonylation reaction mixture following at least one acid extraction may be subjected to further purification or recovery steps which comprise at least one distillation step for separating volatile constituents. For example, a carbonylation reaction mixture comprising phenol, diphenyl carbonate, and an activating solvent such as a polyether may be distilled to separate and recover these components based on differences in their effective boiling points under the distillation conditions. Following recovery, reaction components such as aromatic hydroxy compound and activating solvent may be recycled in further carbonylation reaction mixtures.

Aqueous extracts from carbonylation reaction mixtures may be treated by known methods to recover metals and other constituents that may be present in the aqueous phase. Such methods may comprise one of more of precipitation steps and of extraction steps, for example, as is disclosed in U.S. Pat. Nos. 5,981,788, 6,090,737, 6,143,937, and 6,191,060, assigned to the assignee of the present invention. Recovered metals may be recycled in further carbonylation reaction mixtures, if necessary after conversion by known methods to active forms for catalysis.

The following examples are included to provide additional guidance to those skilled in the art in practicing the claimed invention. While some of the examples are illustrative of various embodiments of the claimed invention, others are comparative. The examples provided are merely representative of the work that contributes to the teaching of the present application. Accordingly, these examples are not intended to limit the invention, as defined in the appended claims, in any manner. In the following examples, the aromatic carbonate produced was diphenyl carbonate (DPC), the Group 8, 9, or 10 metal utilized was palladium, and the activating solvent was a polyether.

General Carbonylation Reaction Conditions Carbonylation reactions were performed using a mixture of catalyst components combined with approximately 60 grams (g) phenol in a sealed reactor at a pressure in a range of between about 7.6 megapascals and about 11 megapascals under a mixture of 9% oxygen in carbon monoxide at 100° C. for a time in a range of between 90 minutes and 150 minutes. No sampling of the reaction was done until the reaction was completed. The reaction was then cooled to 60° C., depressurized, and a small sample (1–4 g) was taken for HPLC and GC analysis. An equivalent weight of aqueous acid (at a concentration in a range of between 3% and 9%) was added to the remainder of the reaction mixture in the reactor, and the reactor was resealed and vented. No filtration or decantation of solids was done prior to addition of the acid. While the mixture was rapidly stirred for 30 minutes at 60° C., either oxygen was bubbled through the reaction at atmospheric pressure, or air or nitrogen was retained in the headspace of the reactor at atmospheric pressure as indicated below. The total contents of the mixture were then transferred to a tared jar, and the reactor was rinsed with an additional 30 g of aqueous hydrochloric acid (at a concentration in a range of between 3% and 9%), which was also added to the organic/aqueous mixture in the jar. In some cases the reactor was finally rinsed with acetonitrile and the acetonitrile phase was analyzed separately. The organic and aqueous phases were separated. The organic phase was analyzed for metals either by atomic absorption spectroscopy (AA) or by organics Inductively Coupled Plasma Analysis (ICP). The aqueous layer was analyzed directly by ICP for metals. If a solid was present, it was filtered, dried, and analyzed by ICP.

EXAMPLE 1

A carbonylation reaction was performed using the above procedure with a catalyst package including 17.3 ppm Pd(acac)$_2$; 198 ppm Cu(acac)$_2$; 202 ppm Ti(O)(acac)$_2$; tetraglyme 7.26% by wt; sodium bromide 0.71% by wt; and sodium hydroxide 0.46% by wt (wherein the % values are by weight of the entire reaction mixture). The combined initial starting weight was 63.84 g. After completion, the reaction mixture was treated as described with 9% aqueous hydrochloric acid while sparging with oxygen. The total weight of the combined washed organic mass, aqueous extractant and aqueous rinse was 166.8 g. The aqueous phase readily segregated from the organic phase. The phases were separated and analyzed; the results of metal and polyether analyses on each liquid phase are shown in Table 1.

TABLE 1

| phase | mL phase collected | ppm Pd (wt/vol) | ppm Cu (wt/vol) | ppm Ti (wt/vol) | % phenol | % DPC | % TG |
|---|---|---|---|---|---|---|---|
| organic | 62.8 | <1.0 | <1.0 | 2.4 ± 0.3 | 65.4 | 11.6 | 7.4 |
| aqueous | 112.4 | 8.04 ± 0.22 | 103.5 ± 0.5 | 124.5 ± 2.4 | 2.0 | 0 | 0 |

These values demonstrate removal of 89.2% of the starting level of Pd; 100.3% of the starting level of Cu; 118% of the starting level of Ti; and none of the tetraglyme into the aqueous phase.

EXAMPLE 2

A carbonylation reaction was performed using the above procedure with a catalyst package including 15.9 ppm Pd(acac)$_2$; 206 ppm Cu(acac)$_2$; 210 ppm Ti(O)(acac)$_2$; 7.06% tetraglyme; 0.70% sodium bromide; and 0.52% sodium hydroxide (wherein the % values are by weight of the entire reaction mixture). The combined initial starting weight was 64.63 g. After completion, the reaction mixture was treated as described with 9% aqueous hydrochloric acid while under air retained in the headspace of the reactor at atmospheric pressure. The total weight of the combined washed organic mass, aqueous extractant and aqueous rinse was 301.4 g.

The aqueous phase readily segregated from the organic phase. The phases were separated and analyzed; the results of metal and polyether analyses on each liquid phase are shown in Table 2.

TABLE 2

| phase | mL phase collected | ppm Pd (wt/vol) | ppm Cu (wt/vol) | ppm Ti (wt/vol) | % phenol | % DPC | % TG |
|---|---|---|---|---|---|---|---|
| organic | 59.6 | <1 | <2.2 | 16.5 ± 1 | 66.2 | 10.1 | 7.5 |
| aqueous | 222.7 | 3.24 ± 0.08 | 44.4 ± 1.2 | 48.3 ± 0.2 | 0.4 | 0 | 0 |

These values demonstrate removal of 80.0% of the starting level of Pd; 84.8% of the starting level of Cu; 90.5% of the starting level of Ti; and none of the tetraglyme into the aqueous phase from a single extraction.

EXAMPLE 3

A carbonylation reaction was performed using the above procedure with a catalyst package including 14.2 ppm Pd(acac)$_2$; 191 ppm Cu(acac)$_2$; 194 ppm Ti(O)(acac)$_2$; 6.9% tetraglyme; 0.65% sodium bromide; and 0.48% sodium hydroxide (wherein the % values are by weight of the entire reaction mixture). The combined initial starting weight was 64.9 g. After completion, the reaction mixture was treated as described with 3% aqueous hydrochloric acid while under air retained in the headspace of the reactor at atmospheric pressure. The total weight of a first extraction (organic mass, aqueous extractant and aqueous rinse) was 122.6 g. Once the phases from the first extraction were separated, most of the organic phase (54.2 g) was returned to the reactor for a second extraction, using 30.4 g of 3% hydrochloric acid while under air retained in the headspace of the reactor at atmospheric pressure.

Following both extractions, the aqueous phase readily segregated from the organic phase. The phases were separated and analyzed; the results of metal and polyether analyses are shown in Table 3.

TABLE 3

| phase | mL phase collected | ppm Pd (wt/vol) | ppm Cu (wt/vol) | ppm Ti (wt/vol) | % phenol | % DPC | % TG |
|---|---|---|---|---|---|---|---|
| Org., 1$^{st}$ ext | 60.9 | <1 | <1.1 | 29.9 ± 0.9 | 64.8 | 8.1 | 5.6 |
| Org., 2$^{nd}$ ext | 47.4 | <1 | <1.1 | 12.3 ± 0.9 | 63.5 | 8.0 | 5.7 |

TABLE 3-continued

| phase | mL phase collected | ppm Pd (wt/vol) | ppm Cu (wt/vol) | ppm Ti (wt/vol) | % phenol | % DPC | % TG |
|---|---|---|---|---|---|---|---|
| Aq., 1st ext | 108.1 | 6.71 ± 0.1 | 100.3 ± 0.73 | 103.9 ± 0.73 | 2.3 | 0 | 0 |
| Aq., 2nd ext | 41.9 | <0.2 | 0.6<x<2.4 | 13.8 ± 0.3 | 4.3 | 0 | 0 |

These values demonstrate removal of 89.2% of the starting level of Pd; 99.4% of the starting level of Cu; 101.1% of the starting level of Ti; and none of the tetraglyme into the aqueous phase in the first extraction. Under similar conditions using half the weight of aqueous acid extractant, no further Pd or Cu (within the analytical detection limits) was removed in a second extraction, while 5.8% more Ti was removed in a second extraction. Again, tetraglyme remained entirely in the organic phase.

EXAMPLE 4

A carbonylation reaction was performed using the above procedure with a catalyst package including 15.29 ppm Pd(acac)$_2$; 190.85 ppm Cu(acac)$_2$; 194.54 ppm Ti(O)(acac)$_2$; tetraglyme 6.9% by wt; sodium bromide 0.66% by wt; and sodium hydroxide 0.55% by wt (wherein the % values are by weight of the entire reaction mixture). The combined initial starting weight was 64.55 g. The extraction procedure was performed using 3% hydrobromic acid, wherein the combined mixture in the reactor was purged three times with nitrogen at about 1 megapascal, depressurized to atmospheric pressure under nitrogen, and then resealed prior to stirring. Only residual nitrogen was present over the mixture. The total weight of the combined washed organic mass, aqueous extractant and aqueous rinse was 123.32 g.

The aqueous phase segregated readily from the organic phase. The phases were separated and analyzed; the results of metal analyses on each liquid phase are shown in Table 4.

TABLE 4

| phase | Wt. phase collected | ppm Pd (wt/vol) | ppm Cu (wt/vol) | ppm Ti (wt/vol) | % phenol | % DPC | % TG |
|---|---|---|---|---|---|---|---|
| organic | 69.73 | <0.5 | <1.6 | 135.7 ± 0.4 | 59.8% | 11.8% | — |
| aqueous | 53.13 | 16.9 ± 0.5 | 204 ± 2.0 | 167 ± 1.0 | 5.0% | 0% | 0% |

These values demonstrate removal of 92.4% of the starting level of Pd; 89.3% of the starting level of Cu; 71.7% of the starting level of Ti; and none of the tetraglyme into the aqueous phase.

Small scale reactions (approximately 5 gram scale) were run in a Paar Pressure reactor vessel using glass vials retained in a machined metal block. These vials were fitted with caps perforated with needles to allow for passage of oxygen/carbon monoxide into the vial as well as water vapor out of the vial. Stirring in the mixture was provided via a magnetic stir bar. Although smaller in volume, these reactions contained similar component ratios compared to the larger sized reactions; the other reaction parameters (heat, pressure, gas composition, reaction time) were also the same. No sampling of the reaction was done until the reaction was completed. After completion of the reaction, the reactor vessel was cooled to 60° C. and depressurized. The cooled vials were removed from the Paar reactor and weighed. A small amount of sample was taken (100 mg) for HPLC and GC analysis.

Acid extractions were performed in these reaction vials in a heated metal block in a heating I stirring unit by the following procedure. Each of the vials was pre-heated in the heating block; separate vials containing equal weight amounts of the acid extractant were pre-heated as well. At time=0, the pre-weighed, pre-heated acid was added to the pre-weighed reaction mixture, a tube bubbling air (equipped with a vent) into the mixture was fitted onto the top of the vial, and stirring was commenced. The temperature of the unit was held constant at 60° C. or 85° C. during the 5 minute stirred extraction. At the end of 5 minutes, the vial was removed from the block, recapped and weighed. After 5 minutes settling time, the phases were separated via pipette into tared vials. Each layer was analyzed for metals by ICP.

EXAMPLE 5

Small scale carbonylation reactions were performed using the above procedure with a catalyst package including 14.01 ppm Pd(acac)$_2$; 41.8 ppm Cu(acac)$_2$; 94.5 ppm Ti(O)(acac)$_2$; tetraglyme 6.1% by wt; sodium bromide 0.6% by wt; and sodium hydroxide 1.4% by wt (wherein the % values are by weight of the entire reaction mixture). Extractions were performed at 60° C. using 3% hydrobromic acid and an air sparge. Replicates were done and are reported as separate vials. The phases were separated and analyzed; the results of metal analyses on each liquid phase are shown in Table 5.

TABLE 5

| phase | Wt. phase collected | ppm Pd (wt/vol) | ppm Cu (wt/vol) | ppm Ti (wt/vol) | % phenol | % DPC | % TG |
|---|---|---|---|---|---|---|---|
| Org. (vial 1) | 5.92 | <0.5 | <1.6 | 48.1 | — | — | — |
| (vial 2) | 5.95 | <0.5 | <1.6 | 47.9 | | | |
| Aq. (vial 1) | 4.01 | 19.4 ± 0.5 | 63.4 ± 1.2 | 127 ± 1.0 | 6.5% | 0% | 0% |
| (vial 2) | 4.14 | 19.2 ± 0.5 | 64.4 ± 1.2 | 138 ± 1.0 | 6.5% | 0% | 0% |

These values demonstrate removal of 104% of the starting level of Pd; 114% of the starting level of Cu; 101% of the starting level of Ti; and none of the tetraglyme into the aqueous extractant. Both Pd and Cu were below the detection limit in the organic phase.

EXAMPLE 6

Small scale carbonylation reactions were performed using the above procedure with a catalyst package including 14.01 ppm Pd(acac)$_2$; 41.8 ppm Cu(acac)$_2$; 94.5 ppm Ti(O)(acac)$_2$; tetraglyme 6. 1% by wt; sodium bromide 0.6% by wt; and sodium hydroxide 1.4% by wt (wherein the % values are by weight of the entire reaction mixture). Extractions were performed at 85° C. using 3% hydrobromic acid and an air sparge. Replicates were done and are reported as separate vials. The phases were separated and analyzed; the results of metal analyses on each liquid phase are shown in Table 6.

TABLE 6

| phase | Wt. phase collected | ppm Pd (wt/vol) | ppm Cu (wt/vol) | ppm Ti (wt/vol) | % phenol | % DPC | % TG |
|---|---|---|---|---|---|---|---|
| Org. | | | | | | | |
| (vial 1) | 6.18 | <0.5 | <1.6 | — | — | — | — |
| (vial 2) | 6.16 | <0.5 | <1.6 | — | — | — | — |
| Aq. | | | | | | | |
| (vial 1) | 3.56 | 22.7 ± 0.5 | 72.2 ± 1.6 | — | 6.5% | 0% | 0% |
| (vial 2) | 3.60 | 23.5 ± 0.5 | 74.1 ± 1.2 | — | 6.5% | 0% | 0% |

These values demonstrate removal of 104–108% of the starting level of Pd; 111–115% of the starting level of Cu; and none of the tetraglyme into the aqueous extractant. Both Pd and Cu were below the detection limit in the organic phase.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims. All of the U.S. Patents mentioned herein are incorporated herein by reference.

What is claimed is:

1. A method for recovering a substantially water-soluble solvent and at least one metal from an organic reaction mixture comprising at least about 35% by weight aromatic hydroxy compound, which comprises the steps of: (i) contacting a reaction mixture at least once with aqueous acid, (ii) mixing the organic and aqueous phases in the presence of an oxygen source, (iii) separating the organic and aqueous phases wherein said solvent remains substantially in the organic phase; (iv) recovering metal species from the aqueous phase; and (v) recovering said solvent from the organic phase.

2. The method of claim 1 wherein the reaction mixture comprises at least about 40% by weight aromatic hydroxy compound.

3. The method of claim 2 wherein the reaction mixture comprises at least about 45% by weight aromatic hydroxy compound.

4. The method of claim 1 wherein the reaction mixture further comprises an aromatic carbonate.

5. The method of claim 4 wherein the reaction mixture comprises phenol and diphenyl carbonate.

6. The method of claim 5 wherein the reaction mixture comprises at least about 40% by weight phenol.

7. The method of claim 6 wherein the reaction mixture comprises at least about 45% by weight phenol.

8. The method of claim 1 wherein the mixture comprises at least one solvent selected from the group consisting of polyethers, nitrites, carboxylic acid amides, and sulfones, and mixtures thereof.

9. The method of claim 8 wherein the solvent is at least one polyether.

10. The method of claim 9 wherein at least one polyether is selected from the group consisting of diethylene glycol dialkyl ethers, diethylene glycol dimethyl ether, triethylene glycol dialkyl ethers, triethylene glycol dimethyl ether, tetraethylene glycol dialkyl ethers, tetraethylene glycol dimethyl ether, polyethylene glycol dialkyl ethers, polyethylene glycol dimethyl ether, crown ethers, 15-crown-5, 18-crown-6, diethylene glycol diphenyl ether, and benzo-18-crown-6.

11. The method of claim 1 wherein the mixture comprises at least one Group 8, 9, or 10 metal and at least one metal cocatalyst different from Group 8, 9, or 10 metals.

12. The method of claim 11 wherein at least one Group 8, 9, or 10 metal is palladium.

13. The method of claim 11 wherein the metal cocatalyst is at least one member selected from the group consisting of lead, copper, titanium, cobalt, manganese, zinc, bismuth, zirconium, tungsten, chromium, nickel, iron, lanthanide metals, cerium, and ytterbium, and mixtures thereof.

14. The method of claim 13 wherein the metal co-catalyst is at least one member selected from the group consisting of lead, cobalt, copper, titanium, manganese, cerium, and mixtures thereof.

15. The method of claim 1 wherein the metals recovered are palladium and at least one of lead, cobalt, copper, titanium, manganese, cerium, and mixtures thereof.

16. The method of claim 1 wherein the reaction mixture further comprises at least one salt.

17. The method of claim 16 wherein the salt comprises an anion selected from the group consisting of tetrafluoroborate, hexafluorophosphate, nitrate, carboxylate, acetate, benzoate, sulfate, halide, chloride, and bromide.

18. The method of claim 17 wherein the salt comprises a cation selected from alkali metals.

19. The method of claim 18 wherein the salt is at least one member selected from the group consisting of sodium chloride and sodium bromide.

20. The method of claim 17 wherein the acid comprises a counterion which is identical to the anion of a salt present in the reaction mixture.

21. The method of claim 1 wherein the acid is at least one inorganic acid.

22. The method of claim 21 wherein the concentration of at least one inorganic acid in water is in a range of between about 0.5% and about 20% by weight.

23. The method of claim 22 wherein the concentration of at least one inorganic acid in water is in a range of between about 0.5% and about 15% by weight.

24. The method of claim 21 wherein the acid is at least one member selected from the group consisting of hydrochloric acid and hydrobromic acid.

25. The method of claim 1 wherein an aqueous acid extraction is performed at a temperature in a range of between about 50° C. and about 100° C.

26. The method of claim 1 wherein contacting a carbonylation reaction mixture at least once with aqueous acid is performed in the carbonylation reactor.

27. The method of claim 1 wherein greater than about 98% of the solvent remains in the organic phase.

28. The method of claim 1 wherein the reaction mixture following at least one aqueous acid extraction is subjected to further purification steps which comprise at least one distillation step.

29. The method of claim 13 wherein the reaction mixture following at least one aqueous acid extraction is subjected to further purification steps which comprise at least one distillation step.

30. The method of claim 29 wherein phenol, diphenyl carbonate, and at least one solvent are separated by distillation.

31. The method of claim 30 wherein at least one solvent is a polyether.

32. A method for recovering a polyether and at least one metal from a carbonylation reaction mixture comprising diphenyl carbonate, an alkali metal salt, and at least about 35% by weight phenol, which comprises the steps of: (i) contacting a carbonylation reaction mixture at least once with aqueous acid, (ii) mixing the organic and aqueous phases in the presence of an oxygen source, (iii) separating the organic and aqueous phases wherein the polyether remains substantially in the organic phase; (iv) recovering metal species from the aqueous phase; and (v) recovering polyether from the organic phase.

wherein the polyether is at least one member selected from the group consisting of diethylene glycol dialkyl ethers, diethylene glycol dimethyl ether, triethylene glycol dialkyl ethers, triethylene glycol dimethyl ether, tetraethylene glycol dialkyl ethers, tetraethylene glycol dimethyl ether, polyethylene glycol dialkyl ethers, polyethylene glycol dimethyl ether, crown ethers, 15-crown-5, 18-crown-6, diethylene glycol diphenyl ether, and benzo-18-crown-6; and wherein the metal is at least one member selected from the group consisting of palladium, lead, copper, titanium, cobalt, manganese, zinc, bismuth, zirconium, tungsten, chromium, nickel, iron, lanthanide metals, cerium, and ytterbium.

33. The method of claim 32 wherein the reaction mixture comprises at least about 40% by weight phenol.

34. The method of claim 33 wherein the reaction mixture comprises at least about 45% by weight phenol.

35. The method of claim 32 wherein the salt is at least one member selected from the group consisting of sodium chloride and sodium bromide.

36. The method of claim 32 wherein the polyether is tetraglyme.

37. The method of claim 36 wherein greater than about 98% of the tetraglyme remains in the organic phase.

38. The method of claim 37 wherein essentially all of the tetraglyme remains in the organic phase.

39. The method of claim 32 wherein the reaction mixture following at least one aqueous acid extraction is subjected to further purification steps which comprise at least one distillation step.

40. The method of claim 39 wherein phenol, diphenyl carbonate, and polyether are separated by distillation.

41. The method of claim 40 wherein the polyether is tetraglyme.

42. The method of claim 32 wherein the metals removed are palladium and at least one of lead, copper, titanium, and mixtures thereof.

43. The method of claim 42 wherein greater than about 80% of the metals are removed from the reaction mixture.

44. The method of claim 32 wherein contacting a carbonylation reaction mixture at least once with aqueous acid is performed in the carbonylation reactor.

* * * * *